United States Patent [19]

Acker

[11] Patent Number: 4,490,306

[45] Date of Patent: Dec. 25, 1984

[54] PREPARATION OF SULFONAMIDES

[75] Inventor: Rolf-Dieter Acker, Leimen, Fed. Rep. of Germany

[73] Assignee: BASF Aktiengesellschaft, Ludwigshafen, Fed. Rep. of Germany

[21] Appl. No.: 458,636

[22] Filed: Jan. 17, 1983

[30] Foreign Application Priority Data

Feb. 6, 1982 [DE] Fed. Rep. of Germany ....... 3204168

[51] Int. Cl.$^3$ ............................................ C07C 143/86
[52] U.S. Cl. ........................... 260/465 E; 260/465 H; 260/465.5 R; 564/79
[58] Field of Search ...... 564/79; 260/465 E, 465.5 R, 260/465 H

[56] References Cited

U.S. PATENT DOCUMENTS

3,147,305  9/1964  Lafferty et al. ....................... 564/79
3,336,382  8/1967  Pearson et al. ....................... 564/79

FOREIGN PATENT DOCUMENTS

1493486  11/1969  Fed. Rep. of Germany ........ 564/79

*Primary Examiner*—Thomas A. Waltz
*Attorney, Agent, or Firm*—John H. Shurtleff

[57] ABSTRACT

Sulfonamides are prepared by reacting ammonia or an amine with a halosilane and then reacting the resulting silylamine with sulfuryl chloride in the presence of a solvent which is inert under the reaction conditions.

The sulfonamides are used as intermediates for drugs and crop protection agents, and are starting materials for the preparation of alkylamidosulfonyl chlorides.

16 Claims, No Drawings

PREPARATION OF SULFONAMIDES

The present invention relates to a process for the preparation of sulfonamides by reacting ammonia or an amine with a halosilane and then reacting the resulting silylamine with sulfuryl chloride in the presence of a solvent which is inert under the reaction conditions.

It has been disclosed that sulfonamides may be prepared by heating an amine with a sulfamide for a relatively long time (A.M. Paquin, Angew. Chem., 60 (1948), 316–320).

Moreover, sulfonamides can be prepared by reacting an amidosulfonyl chloride with an amine (G. A. Benson and W. J. Spillane, Chem. Rev. 80 (1980), 151–186, in particular 173).

I have found that sulfonamides of the formula

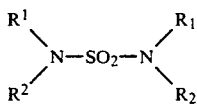
                     I where the individual radicals $R^1$ and $R^2$ are identical or different and are each an aliphatic, cycloaliphatic, araliphatic or aromatic radical or hydrogen, are advantageously obtained by reacting a sulfonyl halide with a nitrogen compound, if (a) ammonia or an amine of the formula

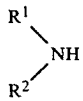
                     II where $R^1$ and $R^2$ have the above meanings, is reacted with a halosilane of the formula

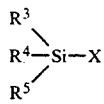
                     III where $R^3$, $R^4$ and $R^5$ are identical or different and are each an aliphatic or aromatic radical or halogen, and X is halogen, and (b) the resulting silylamine of the formula

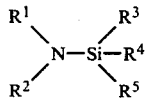
                     IV where $R^1$, $R^2$, $R^3$, $R^4$ and $R^5$ have the above meanings, is reacted with sulfuryl chloride in the presence of a solvent which is inert under the reaction conditions. Where methylamine, trimethylchlorosilane and sulfuryl chloride are used, the process according to the invention can be represented by the following equations:

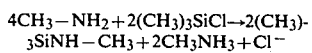

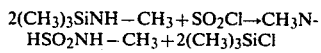

Compared to the conventional processes, the process according to the invention gives sulfonamides in good yield and purity and by a simpler and more economical route. Relatively expensive starting materials, such as sulfamides or amidosulfonyl chlorides, are avoided, and the halosilanes employed in the novel process can be reused.

The starting materials II and III can be employed in stoichiometric amounts, or one of them can be employed in excess, based on the other; advantageously from 1.0 to 4.0, preferably from 1.6 to 2.4, moles of starting material II are used per mole of starting material III. Where an auxiliary base is used, advantageously from 0.5 to 2, preferably from 0.8 to 1.2, moles of starting material II are employed per mole of starting material III, the amount of auxiliary base being advantageously from 0.5 to 3.0, in particular from 0.8 to 1.5, equivalents per mole of starting material III.

Preferred starting materials II and III and substances IV, and accordingly end products I, are those of the formulae where the individual radicals $R^1$ and $R^2$ are identical or different and are each an alkenyl radical of 2 to 7 carbon atoms or an alkyl radical of 1 to 7 carbon atoms which is unsubstituted or substituted by chloroalkyl, thioalkyl, alkoxy of 1 to 4 carbon atoms, cyanoalkyl of 2 to 5 carbon atoms or dialkylaminoalkyl where each alkyl on the nitrogen atom is of 1 to 4 carbon atoms, or are each cycloalkyl of 5 to 8 carbon atoms, or aralkyl or alkylaryl, each of 7 to 12 carbon atoms, or phenyl which is unsubstituted or substituted by 1 or 2 chlorine atoms, bromine atoms, alkyl or alkoxy groups, each of 1 to 4 carbon atoms, nitro groups and/or cyano groups, or are each hydrogen, $R^3$, $R^4$ and $R^5$ are identical or different and are each alkyl of 1 to 7 carbon atoms, or phenyl which is unsubstituted or substituted by 1 or 2 chlorine atoms, bromine atoms, alkyl or alkoxy groups, each of 1 to 4 carbon atoms, nitro groups and/or cyano groups, or are each bromine or, in particular, chlorine, and X is bromine or, in particular, chlorine. The above radicals can be further substituted by groups which are inert under the reaction conditions, eg. alkyl or alkoxy, each of 1 to 4 carbon atoms.

Thus, examples of suitable starting materials II are methylamine, ethylamine, propylamine, isopropylamine, butylamine, isobutylamine, sec.-butylamine, tert.-butylamine, cyclohexylamine, cyclopentylamine, benzylamine, phenylamine, ammonia, N-propyl-N-ethylamine, N-methylaniline, dimethylamine, diethylamine, dipropylamine, diisopropylamine, dibutylamine, di-tert.-butylamine, di-sec.-butylamine, diisobutylamine, dicyclohexylamine, dicyclopentylamine, dibenzylamine, diphenylamine, allylamine, methoxymethylamine, methoxyethylamine, methoxypropylamine, chloromethylamine, chloroethylamine, chloropropylamine, cyanoethylamine, methyl-thioethylamine, N,N-dimethylaminoethylamine and N,N-dimethylamnopropylamine.

Thus, examples of suitable starting materials III are trimethylchlorosilane, triethylchlorosilane, tripropylchlorosilane, triisopropylchlorosilane, tributylchlorosilane, tri-sec.-butylchlorosilane, triisobutylchlorosilane, tri-tert.-butylchlorosilane, methyl-diethylchlorosilane and triphenylchlorosilane, the corresponding chlorosilanes in which 1, 2 or 3 of the other substituents are replaced by chlorine, and the corresponding bromosilanes.

The reaction is carried out as a rule at from $-80°$ to $+100°$ C., in stage (a) advantageously at from $-40°$ to $+100°$ C., in particular from $-20°$ to $+70°$ C., and in stage (b) advantageously at from −80° to +80−° C., in particular from −80° to +60° C., at atmospheric or superatmospheric pressure, continuously or batchwise. Advantageously, solvents which are inert under the reaction conditions are used in both stages. Examples of suitable solvents are halohydrocarbons, in particular chlorohydrocarbons, eg. tetrachloroethylene, 1,1,2,2- and 1,1,1,2-tetrachloroethane, dichloropropane, methylene chloride, dichlorobutane, chloroform, chloronaphthalene, dichloronaphthalene, carbon tetrachloride, 1,1,1- and 1,1,2-trichloroethane, trichloroethylene, pentachloroethane, o-, m- and p-difluorobenzene, 1,2-cis-dichloroethylene, chlorobenzene, fluorobenzene, bromobenzene, iodobenzene, o-, m- and p-dichlorobenzene, o-, m- and p-chlorotoluene and 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and 2,2′-dichlorodiethyl ether, nitrohydrocarbons, eg. nitromethane, nitroethane, nitrobenzene, o-, m- and p-chloronitrobenzene and o-nitrotoluene, nitriles, eg. acetonitrile, butyronitrile, isobutyronitrile, benzonitrile and m-chlorobenzonitrile, aliphatic and cycloaliphatic hydrocarbons, eg. heptane, pinane, nonane and o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, esters, eg. ethyl acetate, ethyl acetoacetate and isobutyl acetate, amides, eg. formamide, methylformamide and dimethylformamide, ketones, eg. acetone and methyl ethyl ketone, and mixtures of such solvents. Advantageously, the solvent is used in an amount of from 100 to 2,000% by weight, preferably from 200 to 700% by weight, based on the weight of the two starting materials II and III together.

The solvents used in each of the two stages may be identical or different. It is also possible to isolate the resulting substance IV after the reaction in stage (a) and then to react this in stage (b). It is more advantageous to carry out a one-pot process without intermediate isolation of substance IV, in which case the total amount of solvent may be introduced in stage (a).

Advantageously, an auxiliary base is used in order to bind the hydrogen halide formed and thus avoid losses of starting material II. Examples of suitable auxiliary bases are trimethylamine, triethylamine, tri-n-propylamine, triisopropylamine, tri-n-butylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-pico-picoline, γ-picoline, isoquinoline, pyrimidine, acridine, N,N,N′,N′-tetramethylethylenediamine, N,N,N′,N′-tetraethylethylenediamine, quinoxaline, quinazoline, N-propyldiisopropylamine, N,N′-dimethylcyclohexylamine, 2,6-lutidine, 2,4-lutidine, trifurylamine and triethylenediamine. Advantageously, from 0.5 to 3.0, in particular from 0.8 to 1.5, equivalents of auxiliary base are used per mole of starting material III.

A stoichiometric amount or an excess of sulfuryl chloride can be employed for the reaction with substance IV; preferably from 0.25 to 1.5 moles, in particular from 0.4 to 0.9 mole, of sulfuryl chloride are used per mole of starting material IV.

The reaction can be carried out by the following procedure. A mixture of starting materials II and III, with or without the auxiliary base and the solvent, is kept at the reaction temperature for from 0.2 to 6 hours in stage (a). Although not absolutely necessary, it is advantageous to carry out the reaction under a protective gas, eg. nitrogen or argon. Advantageously, starting material II in a suitable solvent is initially taken, and starting material III, with or without the auxiliary base, is then added a little at a time. It is also possible for starting material III to be taken initially, and starting material II, with or without the auxiliary base, to be added dropwise. Stage (b) may follow stage (a) without further working up: the reaction temperature in stage (a) is brought to that of stage (b), sulfuryl chloride and, where relevant, the solvent are added, and the reaction is continued for from 0.5 to 8 hours. It is also possible, after stage (a), first to filter the mixture off from the salt and then to continue the reaction, or to purify the resulting silylamine IV by distillation and then to employ it in stage (b). Stage (b) is advantageously carried out either by dissolving the purified silylamine IV in a solvent and adding sulfuryl chloride, or by adding sulfuryl chloride, a little at a time, to the reaction mixture from the silylation reaction at the reaction temperature of stage (b). Advantageously, the mixture is cooled further, for example to −20° C., and then allowed to warm up, for example to 0° C., and stirring is continued for from 2 to 12 hours at room temperature. To bind an excess of amine, a further small amount of starting material III may be added in stage (b). If necessary, the reaction may be continued at a higher temperature, for example from 25° to 60° C., in order to bring it to completion. After the reaction in stage (b) is complete, it is advantageous to distill off starting material III and the solvent, the residue containing the end product I. This may be purified by distillation, recrystallization or extraction. When the procedure is carried out in separate stages with isolation of substance IV, the reaction times are advantageously from 0.2 to 6 hours in stage (a) and from 0.5 to 8 hours in stage (b).

The sulfonamides I are used as intermediates for drugs and crop protection agents, and as starting materials for the preparation of alkylamidosulfonyl chlorides (German published application DAS No. 1,121,060 and German patent No. 1,237,582).

EXAMPLE 1

(a) 70 g of methylamine were condensed at −20° C., and 200 g of xylene, cooled to −20° C., were added. Thereafter, 108.5 g of trimethylchlorosilane were added a little at a time, under nitrogen, and the temperature was kept at from −15° C. to −5° C. The mixture was warmed up to 22° C. and stirring was continued for one hour, after which undissolved material was filtered off, and the methyltrimethylsilylamine was distilled off from the reaction mixture. 63 g of N-methyl-N-trimethylsilylamine of boiling point 66°–70° C./1,005 mbar and $n_D^{23} = 1.3910$ were obtained.

(b) 20.6 g of N-methyl-N-trimethylsilylamine (Example 1a) and 30 g of acetonitrile were combined at −30° C., under nitrogen. 1.1 g of trimethylchlorosilane were added, followed by the addition of 13.5 g of sulfuryl chloride a little at a time, at from −35° to −30° C. Stirring was continued for 15 minutes at −30° C., then for one hour at 0° C. and finally for 5 hours at 22° C. The reaction mixture was evaporated down and the residue was distilled (92°–105° C./0.13 mbar). 8.3 g (73% of theory) of N,N′-dimethylsulfonamide of melting point 69°–72° C. were obtained.

EXAMPLE 2

(a) 118 g of isopropylamine in 300 g of pentane were initially taken, 114.5 g of trimethylchlorosilane were added a little at a time at from 0° to −10° C. under nitrogen, and stirring was continued for one hour at 22° C. The mixture was filtered and then distilled, and 95.6 g of N-isopropyl-N-trimethylsilylamine of boiling point 95°–100° C./1,005 mbar and $n_D^{23} = 1.3941$ were obtained.

(b) A solution of 6.75 g in sulfuryl chloride in 12 g of methylene chloride was added, a little at a time, to 13.1 g of N-isopropyl-N-trimethylsilylamine in 60 g of methylene chloride at from −70° to −75° C., and the mixture was kept for 15 minutes at −75° C. and for one hour at 0° C., and then stirred for a further hour at 22° C. The readily volatile constituents were distilled off, ice water was added to the residue, and the product was filtered off under suction. 12.8 g (71% of theory) of N,N′-diisopropylsulfonamide of melting point 99°–102° C. were obtained.

EXAMPLE 3

29.5 g of isopropylamine and 55.6 g of triethylamine in 320 g of tetrahydrofuran were initially taken, 60 g of trimethylchlorosilane were added a little at a time at from 0° to −5° C. under nitrogen, and stirring was continued for 30 minutes at 22° C. and for one hour at 60° C. The mixture was cooled to −10° C., 33.8 g of sulfuryl chloride were added a little at a time, the mixture was allowed to warm up to 22° C. and stirring was continued for 2 hours. Trimethylchlorosilane and the solvent were distilled off, and the residue was washed with ice water. 30.5 g (68% of theory) of N,N′-diisopropylsulfonamide of melting point 98°–101° C. were obtained.

EXAMPLE 4

49.5 g of cyclohexylamine and 320 g of tetrahydrofuran were initially taken, 32.3 g of dimethyldichlorosilane were added a little at a time at from −5° to 0° C., the mixture was stirred for one hour at 22° C. and then cooled to −30° C., and thereafter 16.9 g of sulfuryl chloride were added a little at a time. The mixture was stirred for 3 hours at 22° C., after which the solvent and the chlorosilane were distilled off and the residue was left to crystallize out and then stirred thoroughly with water. 22 g (67% of theory) of N,N′-dicyclohexylsulfonamide of melting point 151°–153° C. were obtained.

EXAMPLE 5

The reaction was carried out similarly to Example 4, and the results are shown in the Table.

TABLE

| Starting material | | $R^1R^2N-SO_2-NR^1R^2$ | | Yield in % of theory | End product I mp./$n_D$ |
|---|---|---|---|---|---|
| II in g | III in g | $R^1$ | $R^2$ | | |
| 70.0 | 108.5 | CH$_3$— | H | 73 | 69–72 |
| 98.0 | 60.0 | C$_2$H$_5$— | H | 75 | 112 (decomp.) |
| 115 | 113.2 | n-C$_3$H$_7$— | H | 69 | 106–108 |
| 118 | 114.5 | i-C$_3$H$_7$— | H | 71 | 99–102 |
| 73.0 | 120.0 | n-C$_4$H$_9$— | H | 73 | 110–112 |
| 36.5 | 60.0 | s-C$_4$H$_9$— | H | 70 | 61–63 |
| 73.0 | 120.0 | t-C$_4$H$_9$— | H | 71 | 132 (decomp.) |
| 44.5 | 59.8 | CH$_3$OCH$_2$CH$_2$CH$_2$— | H | 79 | 1.4677 |
| 28.5 | 60.0 | CH$_2$=CH—CH$_2$— | H | 65 | 63 (decomp.) |
| 49.5 | 32.3 | cyclohexyl- | H | 67 | 151–153 |
| 46.5 | 60.0 | C$_6$H$_5$— | H | 72 | 105–108 |

I claim:

1. A process for the preparation of a sulfonamide of the formula

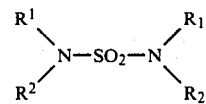   I wherein the individual radicals $R^1$ and $R^2$ are identical or different and are each an aliphatic, cycloaliphatic, araliphatic or aromatic radical or hydrogen, by reacting a sulfonyl halide with a nitrogen compound, wherein
(a) ammonia or an amine of the formula

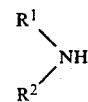   II where $R^1$ and $R^2$ have the above meanings, is reacted with a halosilane of the formala

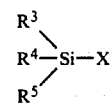   III where $R^3$, $R^4$ and $R^5$ are identical or different and are each an aliphatic or aromatic radical or halogen, and X is halogen, and
(b) the resulting silylamine of the formula

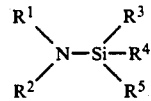   IV where $R^1$, $R^2$, $R^3$, $R^4$ and $R^5$ have the above meanings, is reacted with sulfuryl chloride in the presence of a solvent which is inert under the reaction conditions.

2. A process as claimed in claim 1, wherein the reaction is carried out using from 1 to 4 moles of starting material II per mole of starting material III.

3. A process as claimed in claim 1, wherein, when an auxiliary base is employed, the reaction is carried out using from 0.5 to 2 moles of starting material II per mole of starting material III.

4. A process as claimed in claim 3, wherein the reaction is carried out using from 0.5 to 3.0 equivalents of the auxiliary base per mole of starting material III.

5. A process as claimed in claim 1, wherein the reaction is carried out at from −80° to +100° C.

6. A process as claimed in claim 1, wherein the reaction in stage (a) is carried out at from −40° to +100° C.

7. A process as claimed in claim 1, wherein the reaction in stage (b) is carried out at from −80° to +80° C.

8. A process as claimed in claim 1, wherein the reactions in both stages are carried out using a solvent which is inert under the reaction conditions.

9. A process as claimed in claim 1, wherein the reaction is carried out using from 100 to 2,000% by weight, based on the weight of the two starting materials II and III together, of solvent.

10. A process as claimed in claim 1, wherein the reaction is carried out using from 0.25 to 1.5 moles of sulfuryl chloride per mole of starting material IV.

11. A process as claimed in claim 1, using ammonia or an amine starting material II in which $R^1$ and $R^2$ are identical or different and each represents a substituent selected from the class consisting of:
hydrogen;
alkenyl of 2 to 7 carbon atoms or alkyl of 1 to 7 carbon atoms, each being unsubstituted or further substituted by chloroalkyl, thioalkyl or alkoxy of 1 to 4 carbon atoms in the alkyl group, by cyanoalkyl of 2 to 5 carbon atoms or by dialkylamino where each alkyl on the nitrogen atom has 1 to 4 carbon atoms;
cycloalkyl of 5 to 8 carbon atoms;
aralkyl or alkylaryl, each of 7 to 12 carbon atoms; and
phenyl which is unsubstituted or substituted by 1 or 2 members selected from the group consisting of chlorine, bromine, alkyl or alkoxy each or 1 to 4 carbon atoms, nitro and cyano.

12. A process as claimed in claim 11 using a halosilane starting material III in which X is bromine or chlorine and $R^3$, $R^4$ and $R^5$ are identical or different and each represents a substituent selected from the class consisting of:
bromine;
chlorine;
alkyl of 1 to 7 carbon atoms; and
phenyl which is unsubstituted or substituted by 1 or 2 members selected from the group consisting of chlorine, bromine, alkyl of 1 to 4 carbon atoms, alkoxy of 1 to 4 carbon atoms, nitro and cyano.

13. A process as claimed in claim 12, using a halosilane starting material III in which X is chlorine.

14. A process as claimed in claim 1, wherein the reaction is carried out without intermediate isolation of the silylamine IV from the reaction mixture.

15. A process as claimed in claim 11, wherein the reaction is carried out without intermediate isolation of the silylamine IV from the reaction mixture.

16. A process as claimed in claim 12, wherein the reaction is carried out without intermediate isolation of the silylamine IV from the reaction mixture.

* * * * *